US011409019B1

(12) United States Patent
Gonzales et al.

(10) Patent No.: US 11,409,019 B1
(45) Date of Patent: Aug. 9, 2022

(54) DEVICE FOR PRODUCING HIGH RESOLUTION BACKSCATTER IMAGES

(71) Applicant: Micro-X Limited, Tonsley (AU)

(72) Inventors: Brian Gonzales, Federal Way, WA (US); Robert Charles Sheehy, Ringwood East (AU); Brendan Smith, Tranmere (AU); Brenton Joseph Cardone, St. Morris (AU); Caitlin Sarah Wouters, Athelstone (AU); Shaun Graham, Brighton (AU)

(73) Assignee: MICRO-X LIMITED, Tonsley (Clovelly (AU)

( * ) Notice: Subject to any disclaimer, the term of this patent is extended or adjusted under 35 U.S.C. 154(b) by 0 days.

(21) Appl. No.: 17/234,356

(22) Filed: Apr. 19, 2021

(51) Int. Cl.
*G01N 23/203* (2006.01)
*G01V 5/00* (2006.01)
*G01N 23/20066* (2018.01)

(52) U.S. Cl.
CPC ......... *G01V 5/0025* (2013.01); *G01N 23/203* (2013.01); *G01N 23/20066* (2013.01); *G01N 2223/20* (2013.01); *G01N 2223/401* (2013.01); *G01N 2223/501* (2013.01); *G01N 2223/639* (2013.01)

(58) Field of Classification Search
None
See application file for complete search history.

(56) References Cited

U.S. PATENT DOCUMENTS

| 7,082,182 | B2 | 7/2006 | Zhou et al. | |
|---|---|---|---|---|
| 7,220,971 | B1 | 5/2007 | Chang et al. | |
| 7,227,924 | B2 | 6/2007 | Zhou et al. | |
| 7,245,692 | B2 | 7/2007 | Lu et al. | |
| 7,486,772 | B2 | 2/2009 | Lu et al. | |
| 7,505,562 | B2 | 3/2009 | Dinca et al. | |
| 8,155,262 | B2 | 4/2012 | Zhou et al. | |
| 8,189,893 | B2 | 5/2012 | Zhang et al. | |
| 8,971,484 | B2 | 3/2015 | Beckmann et al. | |
| 9,250,200 | B1* | 2/2016 | Grubsky | G01N 23/046 |
| 9,782,136 | B2 | 10/2017 | Zhou et al. | |
| RE48,612 | E * | 6/2021 | Yun | H01J 35/08 |
| 2004/0218714 | A1 | 11/2004 | Faust | |
| 2005/0117701 | A1* | 6/2005 | Nelson | G01N 23/203 378/87 |
| 2015/0153156 | A1* | 6/2015 | Shah | G01J 3/453 356/456 |
| 2016/0259065 | A1* | 9/2016 | Maad | G01T 1/17 |

(Continued)

*Primary Examiner* — Hoon K Song
(74) *Attorney, Agent, or Firm* — Seed Intellectual Property Law Group LLP

(57) ABSTRACT

An X-ray imaging apparatus comprises a digital X-ray detector housed in a radiation shielded enclosure with multiple pinhole apertures in the front panel of the housing. An X-ray source illuminates a target and X-rays are backscattered towards the X-ray imaging apparatus. The multiple pinhole apertures arranged in a pattern so that each pinhole generates a respective pinhole image on the X-ray detector. The size of each image is controlled by the thickness of the front panel and the width of the pinhole aperture (acting as optical stops), and the distance to the X-ray detector, and these values are selected to prevent overlap between any pair of pinhole images on the X-ray detector. An image processor is used to generate a synthetic combined image of the object form the multiple pinhole images.

13 Claims, 8 Drawing Sheets

(56) References Cited

U.S. PATENT DOCUMENTS

2017/0319160 A1   11/2017  Lu et al.
2017/0329037 A1   11/2017  Zhou et al.
2018/0140265 A1*  5/2018   Chu .................. A61B 6/483

* cited by examiner

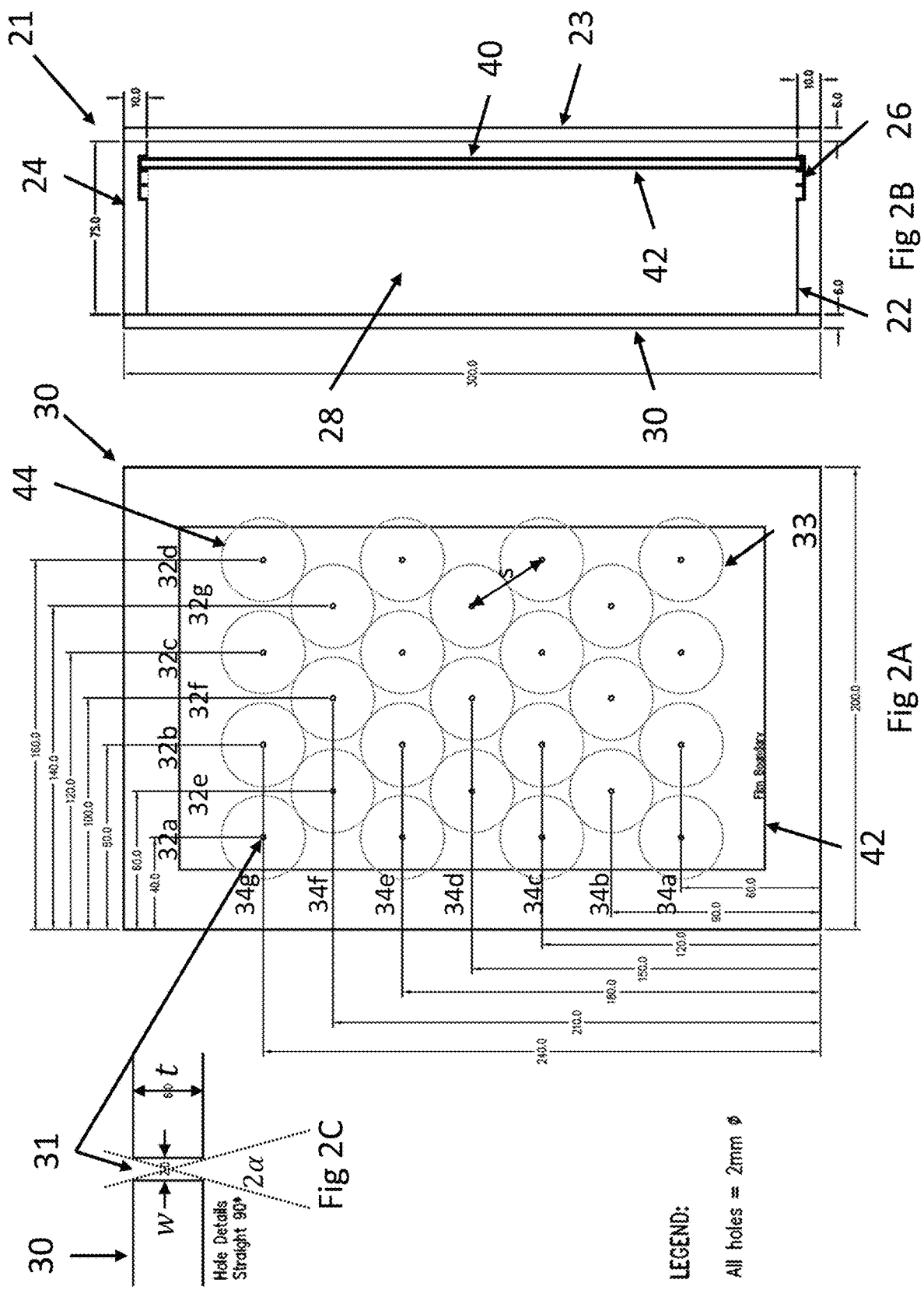

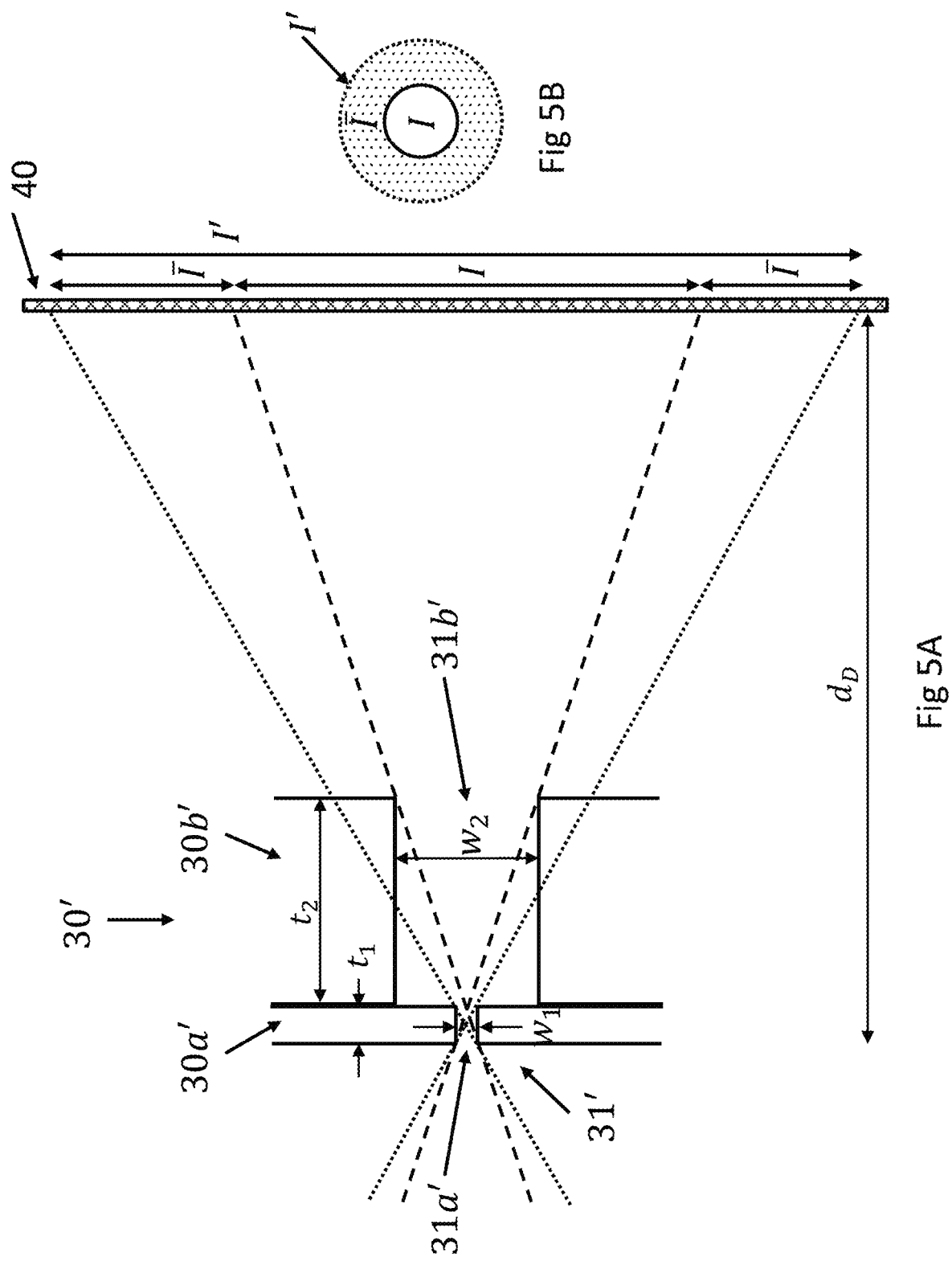

DEVICE FOR PRODUCING HIGH RESOLUTION BACKSCATTER IMAGES

BACKGROUND

Technical Field

Embodiments of the present invention relate generally to X-ray imaging devices and in particular devices for producing X-ray images of objects from backscattered Compton X-ray radiation.

Description of the Related Art

X-ray backscattered Compton radiation is a natural component of X-rays interaction with any material; the strength and direction of the scattered radiation is proportional to the energy of the incident X-rays and the material's atomic composition. Low atomic number materials, particularly carbon-based organic materials, have a high probability of backwards directed Compton scatter when the X-ray energy is range of 40 kVp to 140 kVp. The probability of Compton backscatter is also proportional to the density of the material, materials with densely packed atoms have more atoms to produce backscattered radiation in a given unit area. This makes Compton backscatter imaging particularly useful in imaging dense organic materials such as explosives, narcotics and counterfeit currency. For this reason, backscatter imaging is of interest to explosive ordinance disposal (EOD) technicians, customs and border control officers, and police and other first responders.

X-ray backscattered Compton radiation, even when scattering off a highly efficient material, produces orders of magnitude lower X-ray dose compared with conventional transmission X-ray. Transmission X-ray is a broad spectrum signal and the image on the detector is produced by comparing the intensity of the X-ray signal passing through different materials, each material will attenuate some of the X-ray signal and allow some of the signal through to the detector. Compton backscattered radiation is narrower spectrum signal and the angle of backscatter along with amount of radiation scattered is proportional to the different materials. This makes Compton radiation more specific to materials being imaged but also make it more challenging to gather enough signal to generate a high-quality image.

Conventional X-ray backscatter imaging rely on a large area scintillator coupled to a photomultiplier tube. The large area scintillator collects a wide angle of backscattered radiation and converts it into a very low light signal. The low light signal is increased in strength using a photomultiplier tube and then converted into an electronic signal. This process creates a single backscatter intensity value over a unit of time. To create an image, the X-ray beam is rastered as a thinly collimated pencil beam over the target object and backscatter from the points along the beam are collected as the image intensity at the point in space corresponding in time to the rastered beam location. This process builds a two dimensional X-ray backscatter signal one image pixel at a time. The resolution in the image is dependent on how fast the beam is rastered and the strength of the X-ray beam. If the beam is rastered faster the resolution is low and as the beam is rastered slower the resolution increases. If the strength of the beam is increased, the resolution is increased.

In conventional rastered backscatter imaging, a standard omnidirectional X-ray source is collimated down to a narrow pencil beam in one direction and all the remaining X-ray is absorbed by heavy shielding. The pencil beam collimator is a rotating tungsten or lead collimator with series of small parallel holes to collimate the beam. This standard backscatter architecture means that the X-ray source is either very low power so that it is easy to shield the X-ray beam or the shielding is very complex and heavy. If the X-ray source is low power, the X-ray backscatter signal will be very low and the back-scatter imaging will be low resolution and noisy. If the X-ray source power is higher, the shielding becomes so heavy and complex the imaging can only be used in a fixed installation or large heavy vehicle.

The limitations in conventional X-ray backscatter imaging restrict its widespread application. It would be desirable to a high-resolution light weight backscatter imaging solution for applications including explosive detection and narcotics detection. A lightweight high-resolution backscatter imaging may also have applications in industrial inspection, where imaging of small imperfections in manufactured items is of interest and placing a detector on the opposite side of the item is not feasible.

Another approach that has been proposed is to create an X-ray Compton backscatter image is to use a coded aperture with a large area X-ray detector. A coded aperture is a large area collimator that is placed between the X-ray detector and the imaged objects where the pattern on the aperture collimator limits the directions the X-ray scatter can arrive from and generates multiple overlapping images on a detector. If the pattern of the aperture is known, a three-dimensional estimation of the backscattered signal can be mathematically reconstructed from the total backscatter intensity signal on the detector (e.g. by demultiplexing/deconvoluting the overlapping images based on the known pattern). A simple form of a coded aperture is a plate with multiple pinholes which generates multiple overlapping images on the detector (one image per pinhole). To increase the information content more complex coded apertures have been proposed such as using a grid of pixel coded masks which generate more complex overlapping image patterns on the detector.

Coded aperture Compton scatter imaging has the potential advantage that more of the X-ray signal is used instead being absorbed by the shielding right at the source; this increased efficiency means a higher power X-ray source can be used and substantially less shielding is required. Coded aperture Compton scattering also has the advantage that it provides three-dimensional backscatter imaging instead of just the two dimensional information available in conventional rastered backscatter imaging. However, despite these potential advantages, coded aperture backscatter imaging has not advanced past the level of basic research.

This is largely because the encoded Compton backscatter data captured during coded aperture backscatter imaging is exceptionally challenging to decode as the encoded backscatter signal is overlapping and complex. The signal from any given point on the detector is the sum of all the paths that backscattered radiation could take to get that point, making the problem solution space very large. The problem rapidly becomes underdefined, meaning there are more variables to solve for (image locations to reconstruct) then there are data samples (detector pixels). As such it is not mathematically possible to accurately reconstruct the X-ray backscatter image, and thus (due to the mathematical limitations), coded aperture backscatter imaging result in blurred low-resolution images. This has restricted the use of this approach to basic research in an on-going attempt to find a way around these limitations.

There is thus a need to develop improved methods and apparatus for generating X-ray images from backscattered Compton radiation, or to at least provide a useful alternative to existing methods and apparatus.

SUMMARY

According to a first aspect, there is provided an X-ray imaging apparatus comprising:

a digital X-ray detector comprising an imaging surface;

a radiation shielded enclosure housing the digital X-ray detector and comprising a pinhole panel located in a front surface of the housing with a plurality of pinhole apertures each passing through the panel and having a predefined thickness and a predefined width, wherein the imaging surface is located a separation distance from the pinhole panel, and the radiation shielded enclosure is configured to restrict X-ray radiation incident on the imaging surface to X-rays passing through the plurality of pinhole apertures such that each pinhole aperture generates a respective pinhole image on the imaging surface, and the plurality of pinhole apertures are distributed over the pinhole panel in a predefined pattern and configured such that a diameter of the pinhole image is determined by the separation distance, the thickness and the width of the corresponding pinhole aperture, and the separation distance, thickness, width, and predefined pattern of the pinhole apertures are selected to prevent overlap between any pair of pinhole images on the imaging surface, and in use, an X-ray source illuminates an object located an object distance from the pinhole panel to generate Compton backscattered X-rays towards the X-ray imaging apparatus, and the digital X-ray detector is configured to capture a plurality of pinhole images on the imaging surface which are combined by an image processor to generate a synthetic combined image of the object.

In one form, when in use, the object distance is greater than the separation distance and each pinhole images samples at least a portion of the object and the object distance is selected such that each sample portion overlaps at least one other sample portion.

In one form, the X-ray imaging apparatus may further comprise the image processor which is configured to identify each of the plurality of pinhole images in an image captured by the digital X-ray detector and generate the synthetic combined image of the object by combining the plurality of pinhole images.

In one form, the apparatus may further comprise a distance sensor or proximity sensor configured to determine the object distance from the pinhole panel and the object, and the object distance is provided to the image processor for use in generating the synthetic combined image.

In one form, the image processor may be configured to generate the synthetic combined image using an iterative reconstruction approach to account for depth information inherent in the plurality of pinhole images due to a depth of the object.

In one form, the digital X-ray detector may be a CMOS, photon counting, or Photodiode array digital detector.

In one form, the pinhole panel may comprise of multiple stacked pinholes of different widths and thicknesses to balance radiation shielding, image resolution, and pinhole image size on the imaging surface.

In one form, the X-ray source may be configured to illuminate an object located an object distance from the pinhole panel to generate Compton backscattered X-rays towards the X-ray imaging apparatus.

In one form, the X-ray source may be a Carbon Nanotube X-ray source.

According to first aspect, there is provided a method for generating a synthetic combined X-ray image of an object comprising:

illuminating, using an X-ray source, an object located an object distance from an X-ray imaging apparatus to generate Compton backscattered X-rays towards a pinhole panel located in a front surface of the X-ray imaging apparatus;

capturing a plurality of pinhole images on an imaging surface of the X-ray imaging apparatus, wherein the imaging surface is located a separation distance behind the pinhole panel, and the pinhole panel is comprised of a plurality of pinhole apertures, each passing through the pinhole panel and having a predefined thickness and a predefined width, and are distributed over the pinhole panel in a predefined pattern, and the separation distance, thickness, width, and the predefined pattern of the pinhole apertures are selected to prevent overlap between any pair of pinhole images on the imaging surface, and the X-ray imaging apparatus is located such that the object distance is greater than the separation distance so that for at least one pair of pinholes, each pinhole samples an overlapping portion of the object;

obtaining an estimate of the object distance; and generating, by an image processor, a synthetic combined image of the object using the plurality of pinhole images and the separation distance, object distance, pinhole thickness and pinhole width.

In one form obtaining an estimate of the object distance may comprise measuring the object distance using a range finder, distance sensor, proximity sensor or stereoscopic camera.

In one form, the pinhole panel may be comprised of multiple stacked pinholes of different widths and thicknesses selected to balance radiation shielding, image resolution, and pinhole image size on the imaging surface.

In one form, generating the synthetic combined image may be performed using an iterative reconstruction method which takes into account depth information inherent in the plurality of pinhole images due to a depth of the object.

BRIEF DESCRIPTION OF DRAWINGS

Embodiments will now be described in further detail by reference to the accompanying drawings. It is to be understood that the particularity of the drawings does not supersede the generality of the preceding description.

FIG. 2A is front view of an embodiment of an X-ray imaging apparatus comprising a housing forming a radiation shielded enclosure with a front aperture panel comprised of multiple pinhole aperture specifically designed to generate non overlapping images on a digital X-ray detector housed within the radiation shielded enclosure.

FIG. 2B is side view of the radiation shielded enclosure of the housing shown in FIG. 2A.

FIG. 2C is a cross sectional view through a pinhole aperture in the front aperture panel.

FIG. 5A is side view of a composite pinhole in a composite X-ray attenuation plate according to an embodiment.

FIG. 5B is a schematic illustration of the comparative image sizes that would be generated solely by the first pinhole and by the composite pinhole as illustrated in FIG. 5A.

In the following description, like reference characters designate like or corresponding parts throughout the figures.

DETAILED DESCRIPTION

Figure 1A:
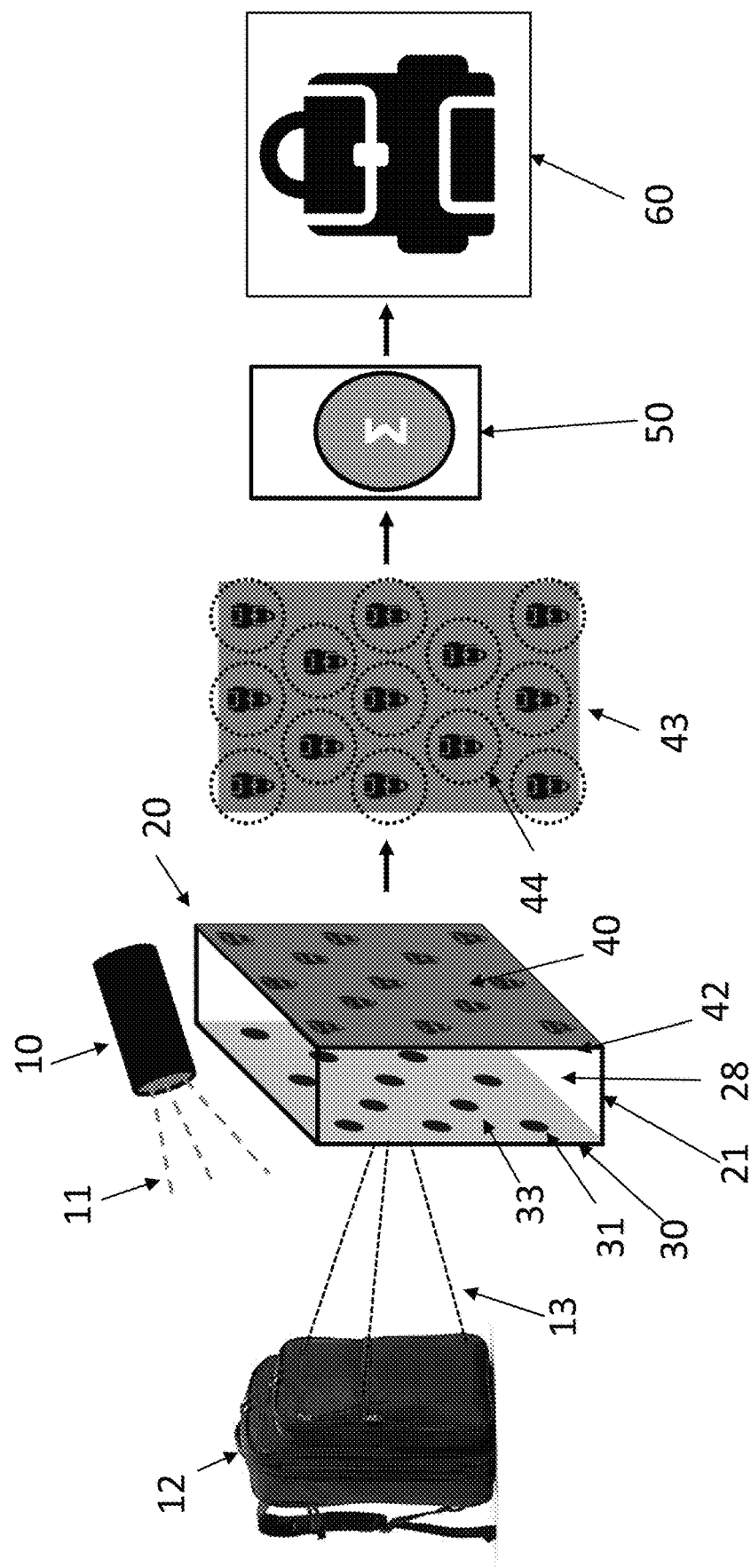
FIG. 1A illustrates a schematic diagram of an embodiment of an X-ray imaging apparatus comprising multiple non-overlapping pinhole apertures and a method of use for generating a high resolution X-ray Compton backscatter image using an aperture plate.
Figure 1B:
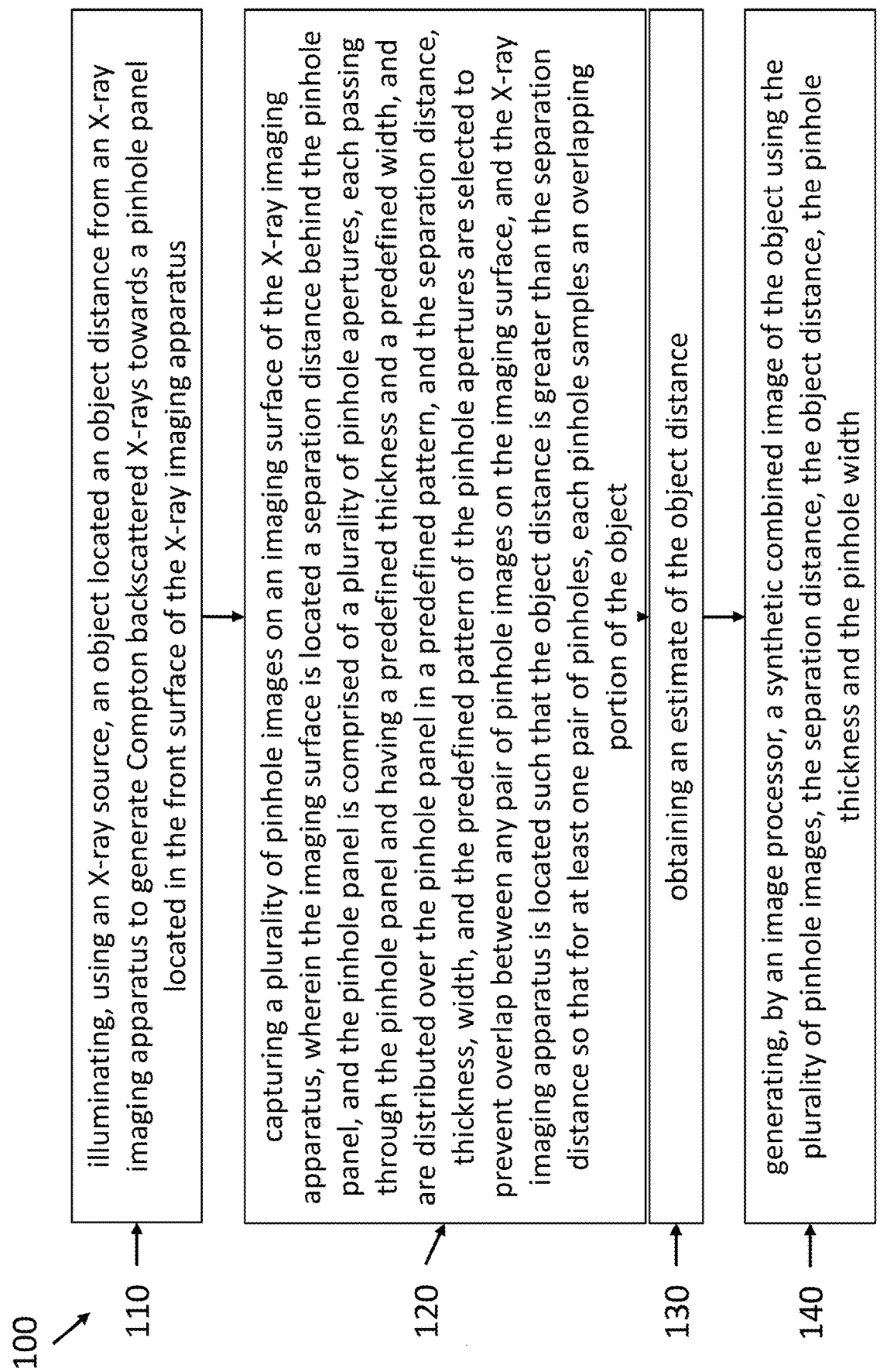
FIG. 1B is a flowchart of a method for generating a synthetic combined X-ray image of an object according to an embodiment.

Referring now to FIG. 1A there is shown an embodiment of an X-ray imaging apparatus 20 used to generate a composite X-ray Compton backscattered image 60 of an object, and FIG. 1B is a flowchart of a method 100 for generating a synthetic combined X-ray image of an object according to an embodiment.

The X-ray imaging apparatus 20 comprises a housing 21 in which a pinhole panel 30, which is comprised of a plurality of pinhole apertures 31, forms at least part of the front surface of the housing. The pinhole panel may be a flat plate, such as a flat metal plate, or be a composite panel. The housing 21 provides or forms a radiation shielded enclosure (or internal cavity) 28 that houses a digital X-ray detector 40 with an imaging surface 42. In use, an X-ray source 10 is used to broadly direct X-rays 11 at an object 12 which is located an object distance $d_O$ from the X-ray imaging apparatus 110. This broadly illuminates the object so the incident flux is either an approximately uniform over the object, or at least known (i.e. so any non-uniformities can be estimated and accounted for). Some of the incident X-rays interact 11 with the object 12 and Compton backscattered X-rays 13 are scattered back towards the X-ray imaging apparatus 20 where they pass through a plurality of pinhole apertures 31 in the pinhole panel 30 to form a plurality of pinhole images 44 on the imaging surface 42.

The pinhole panel 30 is comprised of a plurality of pinhole apertures 31, each passing through the panel and having a predefined thickness t, and a predefined width w. The housing 21 is configured to provide a radiation shielded enclosure 28 (including pinhole panel 30) to restrict X-ray radiation incident on the imaging surface 42 to X-rays passing through the plurality of pinhole apertures 31 such that each pinhole aperture 31 generates a respective pinhole image on the imaging surface 42. The housing 21 may be formed of a radiation shielding material or materials such that the walls define the enclosure 28, or the housing may be lined with a radiation shielding material to form the enclosure 28. Suitable materials include plates of lead, steel or metal alloy of sufficient thickness to block or absorb X-rays. The X-ray detector may also form part of the radiation shielding. That is the radiation shielding only allows backscattered X-rays to enter the enclosure via the pinholes with all other incident X-rays (at least in the energy range generated by the X-ray source) blocked/absorbed by the shielding.

The two-dimensional imaging surface 42 of the digital X-ray detector may be a two-dimensional flat panel digital detector (although a curved panel could be used) and is located a distance, that we will refer to as the separation distance, from the pinhole panel $d_D$. For a given image, the separation distance is a pre-defined, or at least, a known distance. In some embodiments the X-ray imaging apparatus is constructed so that the digital X-ray detector is in a fixed location such as mounted on or in the rear wall of the housing 21 (or the radiation shielded enclosure 28 of the housing) so the separation distance is a fixed distance. In other embodiments the X-ray imaging apparatus 20 is constructed to allow the digital X-ray detector 40 (and thus the imaging surface 42), to be moved with respect to the pinhole panel. This could be implemented using a support structure within the housing 21 (or radiation shielded enclosure of the housing) incorporating one or more motors to translate the digital X-ray detector, and thus the imaging surface. In another embodiment the digital X-ray detector could be designed to allow translation of the imaging surface, e.g., the X-ray detector has a fixed mounting to the housing but allows translation of the imaging surface. In another embodiment the interior of the housing, or the radiation shielded enclosure of the housing, is configured with internal locating or mounting arrangements (e.g. slots, projections, flanges, etc.) to allow location of the digital X-ray detector at one of a number of predefined locations to generate a set of predefined separation distances. Between operations the enclosure could be opened and the digital X-ray detector moved to the desired location, or a mechanism provided to allow movement of the X-ray detector between the different predefined locations. According to optical theory the separation distance can equivalently be considered the focal distance, being the distance from the pinhole where the image is captured.

The diameter and resolution of each pinhole image 44 can be determined based on pinhole optical theory, such as that which applies to visible light pinhole apertures and pinhole cameras. According to pinhole optical theory the image on the detector is a projection through the pinhole, so the further the detector is from the pinhole ($d_D$), the larger the image will be (I). Additionally a pinhole does not create a natural focal point, so the pinhole image remains in focus regardless of the distance from the pinhole to the imaged object ($d_O$), or the distance of the imaging surface from the pinhole ($d_D$). The key difference between visible light pinhole imaging and X-ray backscatter pinhole imaging is in relation to the thickness of the aperture. In visible light the aperture is made in a material as thin as possible. However in X-ray backscatter applications the aperture must be thick enough to block/absorb incoming X-ray radiation, which for practical materials leads to thicknesses of the order of 5 millimeters or more. The walls of the thicker aperture act as an optical stop to restricts the viewing angle (or field-of-view) on the detector and can add to the loss of resolution on the detector. A cross sectional view through a pinhole aperture showing this effect and the viewing angle is shown in FIG. 2C. We can define the viewing angle $2\alpha$ of a pinhole based on the pinhole width w and thickness t according to $$\tan \alpha = w/t. \quad \text{Equation 1}$$

Figure 2D:
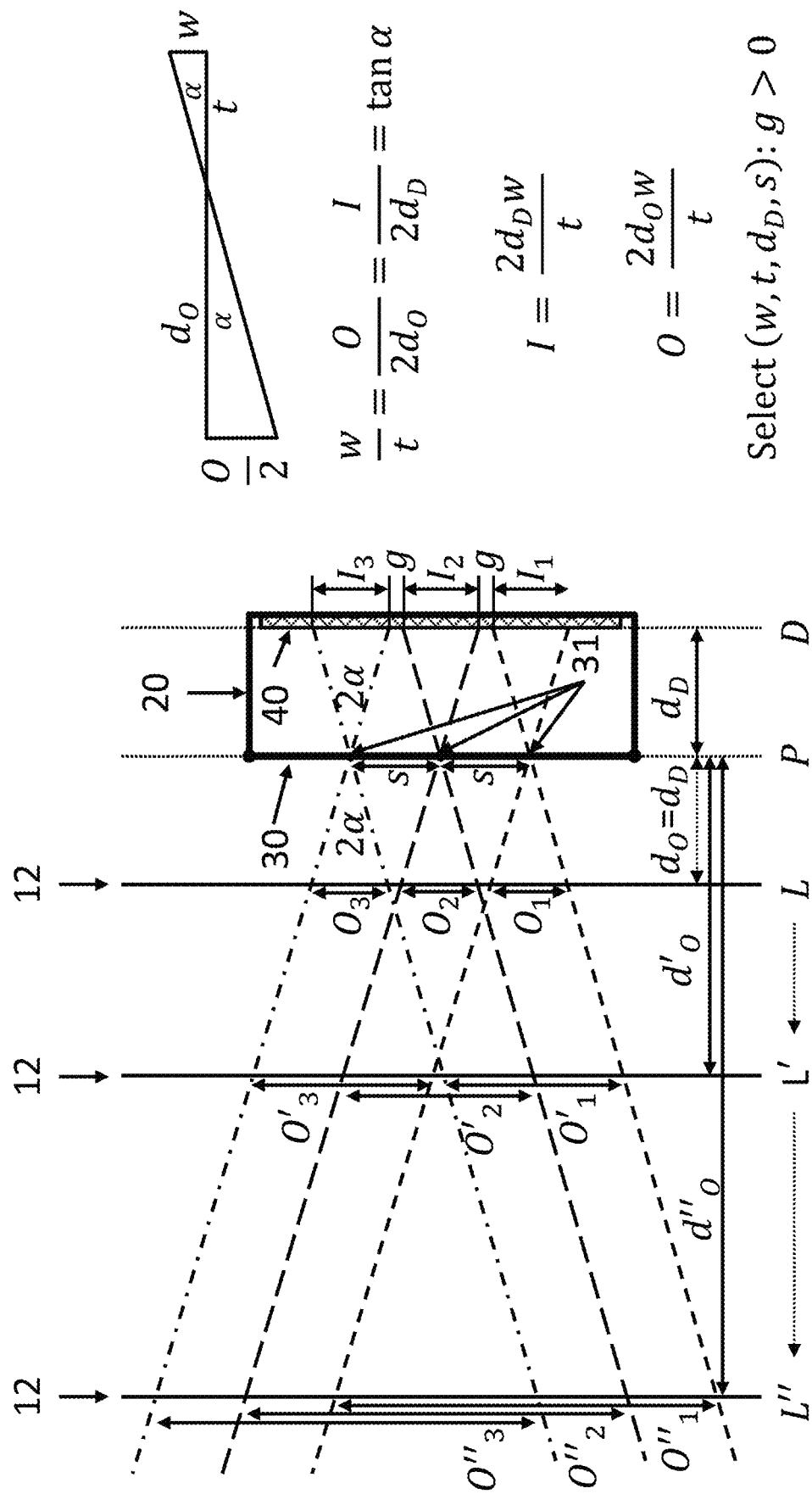
FIG. 2D is a schematic ray tracing diagram showing how non overlapping backscatter images are formed on the digital X-ray detector of an X-ray imaging apparatus according to an embodiment.

With reference to FIG. 2D which is a schematic ray tracing diagram showing formation of pinhole images on the imaging surface, the diameter of the pinhole image, I, can then be determined based on the viewing angle and the distance from the pinhole to the imaging surface using simple trigonometry as $\tan \alpha = (I/2)/d_D = I/2d_D$. This can be rearranged to give the image diameter in terms of pinhole width and thickness:

$$I = 2d_D w/t \quad \text{Equation 2}$$

In some embodiments, the selection of pinhole width will be made based on achieving some desired image size on the detector surface, or a desired number of pixels based on the physical size of detector pixels, together with some desired separation distance or range of separation distances. As X-ray dose decreases sharply with distance, and as many applications are intended for portable or field use, separation distances will often (but need not be) in the range of 10's to 100's of mm. It is noted that the image size may thus also be influenced by the choice of digital detector, and its associated pixel size. That is in some embodiments, particularly where it is desirable to keep costs down, the design process may include selecting a cost effective digital detector which will have some predefined pixel size (e.g. 0.1 mm pixels) along with a desired minimum number of pixels per image, which will effectively set the image size and pinhole width.

The resolution of the image is determined by the width w of the pinhole aperture. If the pinhole has a large width (diameter), there is more uncertainty where light/X-rays are coming from on the object and this causes loss of resolution in the image. If the width is very small diffraction related effects may also affect the resolution. As image size depends upon width, small width will also require use of high resolution digital detectors. Thus in many embodiments where it is desirable to reduce cost or to make the apparatus compact, for example to support portability, the design criteria around choice of detector and separation distance will result in selection of a width which is much larger than the diffraction limit (and thus diffraction effects can be ignored).

A challenge of using X-ray backscatter pinhole apertures is that X-ray dose on the detector from each pinhole is very low. Only a small fraction of the X-ray dose emitted by the source 10 is reflected as backscatter X-rays 13, and only the X-rays that pass through a pinhole 31 end up collected by the detector to make a pinhole image 44. Thus, an individual pinhole aperture is a very inefficient method for collecting X-ray backscatter signal. Thus to increase the dose on the detector a plurality of pinhole apertures 31 are used to general a plurality of pinhole images 44 on the detector 40 (one per pinhole). However in contrast to coded aperture approaches the pinhole apertures are distributed over the pinhole panel in a predefined (or known) pattern where the pattern is selected or designed to specifically prevent overlap between any pair of pinhole images 44 on the imaging surface 42. The digital detector 40 is a large area two dimensional detector, such that the imaging surface 42 captures a separate image 44 of the object for each pinhole 31. An image processor 50 is then used to combine the plurality of pinhole images 44 to generate a synthetic combined image of the object 60 which is provided to the end user.

To further improve the resolution the object is located at an object distance $d_O$ from the pinhole panel 30 which is greater than the distance the detector 40 is from the pinhole panel ($d_D$) 30. The distance the detector 40 is from the pinhole 30 panel ($d_D$) is the focal distance, which we will also refer to as the separation distance, or separate distance (to distinguish it from the object distance). By placing the object at a distance from the pinhole panel greater than the focal distance, each individual pinhole image will sample a different portion of the object. Thus to further improve the resolution of the composite image, the object may be placed at an object distance from the pinhole panel that is greater than the separation (focal) distance $d_D$ and selected such that each sample portion on the object (associated with a pinhole) overlaps at least one other sample portion (associated with another pinhole).

This is further illustrated in FIGS. 2A to 2G. FIG. 2A is front view of an embodiment of the housing 21 formed of steel plates arranged to form the radiation shielded enclosure 28. The front pinhole panel 30 is a flat plate forming the entire front surface of the enclosure 28. FIG. 2B is a side view of the housing 21 shown in FIG. 2A showing the front plate 30, bottom plate 22, rear plate 23 and top plate 24 which form the radiation shielded enclosure 28. In this embodiment the front plate (the pinhole panel) 30 and rear plate 23 are 6 mm thick steel plates, and the top, bottom and side walls (not shown) are each are 10 mm thick steel plates. Slots 26 are machined into the interior side walls to allow placement of a flat area detector at a range of separation distances from the front plate. In this embodiment the housing 21 has a total width of 200 mm, a height of 300 m, and a depth of 87 mm (6 mm each for front 30 and rear 23 plates, with the top and bottom plates having a 75 mm long span) such that the radiation shielded enclosure has dimensions of a width of 180 mm, a height of 280 mm and a depth of 75 mm. In this embodiment the slots 26 allow placement of the imaging surface 42 (and the X-Ray detector) at distances of 46 mm, 52 mm, and 58 mm from the rear surface of the front plate. The housing 21 is configured such that one of the side walls can be (temporarily) removed to allow the X-ray detector to be moved to a new slot to change the location of the imaging surface 42 and thus the separation distance. Once moved the side wall can be placed back and secured to the housing 21 to reform the radiation shielded enclosure 28.

As shown in FIG. 2A a plurality of pinhole apertures 31 are formed in the front panel 30 in a pattern comprised of 4 rows (34a, 34c, 34e and 34g) of 4 pinholes (32a, 32b, 32c and 32d) each interspersed by a row (34b, 34d and 34f) of 3 pinholes (32e, 32f and 32g) to generate 7 rows with a total of 25 pinholes. The first row of pinholes is located 60.0 mm from the bottom edge of the front panel, with each row offset by a further 30 mm. The first column of pinholes is located 40 mm from the left edge, and each column is offset by a further 20 mm. FIG. 2C is a cross sectional view through a pinhole aperture 31 in the front aperture plate. In this embodiment the pinholes are straight cylindrical apertures with a pinhole width (diameter) of 2 mm and pinhole thickness of 6 mm.

This pattern (or distribution) is specifically designed to generate non overlapping images on the imaging surface 42 of a digital X-ray detector (housed in the radiation shielded enclosure 20). That is the plate thickness, pinhole width, pinhole separation distances, and distance of the imaging surface to the pinhole panel selected so that the image 44 generated by each pinhole 31 does not overlap with the images 44 generated from any neighboring pinhole 31. This is illustrated in FIG. 2A which shows the associated diameter (circles) of each pinhole image 44 on the imaging surface 42 with the imaging surface in the rearmost slot within the housing 21. FIG. 2A also shows that the separation distance s between pairs of pinholes on the front plate are selected to exceeds the sum of the radius of two adjacent images.

The pinhole dimensions also define the size of the portion of the object (which we call the sample portion O) that each pinhole (and pinhole image) observes or samples on the object. This is illustrated in FIG. 2D which is a schematic ray tracing diagram showing how non overlapping backscatter images 44 are formed on the imaging surface 42 of the digital X-ray detector 40 from pinholes 31 for three different object distances $d_O$ of the object in front of the pinhole panel 30. As shown in FIG. 2D for an object at some object distance $d_O$ in front of pinhole panel 30, we can extend the rays of the viewing angle onto the object, and using the object distance $d_O$, pinhole width w, pinhole thickness t and similar triangles to give the size of the object sample O:

$$O=2d_O w/t \qquad \text{Equation 3}$$

The object 12 is shown as an extended object, and in the first case, the object is located at a location L which the same distance in front of the pinhole panel as the detector is from the pinhole panel (i.e. $d_D=d_O$). Each of the three pinholes generates a separate image $I_1$, $I_2$, and $I_3$ on, the imaging surface 42, with the size of the image determined using Equation 2, and the separation s of pinholes selected so that there is a gap g between each image on the imaging surface 42. In the first case each of the pinholes sample a different portion of the object $O_1$, $O_2$, and $O_3$, such that each image is sampling a different portion of the object (there is no sample overlap on the object). However as we progressively moved the object further away to location L' at distances $d'_O$ we see that the size of the sample portions on the object $O'_1$, $O'_2$, and $O'_3$, increase and overlap, so that pinhole images $I_1$ and $I_2$ share overlapping portion of the object (overlap of $O'_1$ and $O'_2$) pinhole images $I_2$ and $I_3$ share overlapping portion of the object (overlap of $O'_2$ and $O'_3$). Similarly if we further increase the object further away to location L" at distances $d''_O$ we see that the size of the sample portions on the object $O''_1$, $O''_2$, and $O''_3$, further increase and the amount of overlap increase, so that all pinhole images $I_1$, $I_2$ and $I_3$ share overlapping portion of the object (overlap of $O'_1$ $O'_2$ and $O'_3$).

Figures 2E, 2F, 2G:
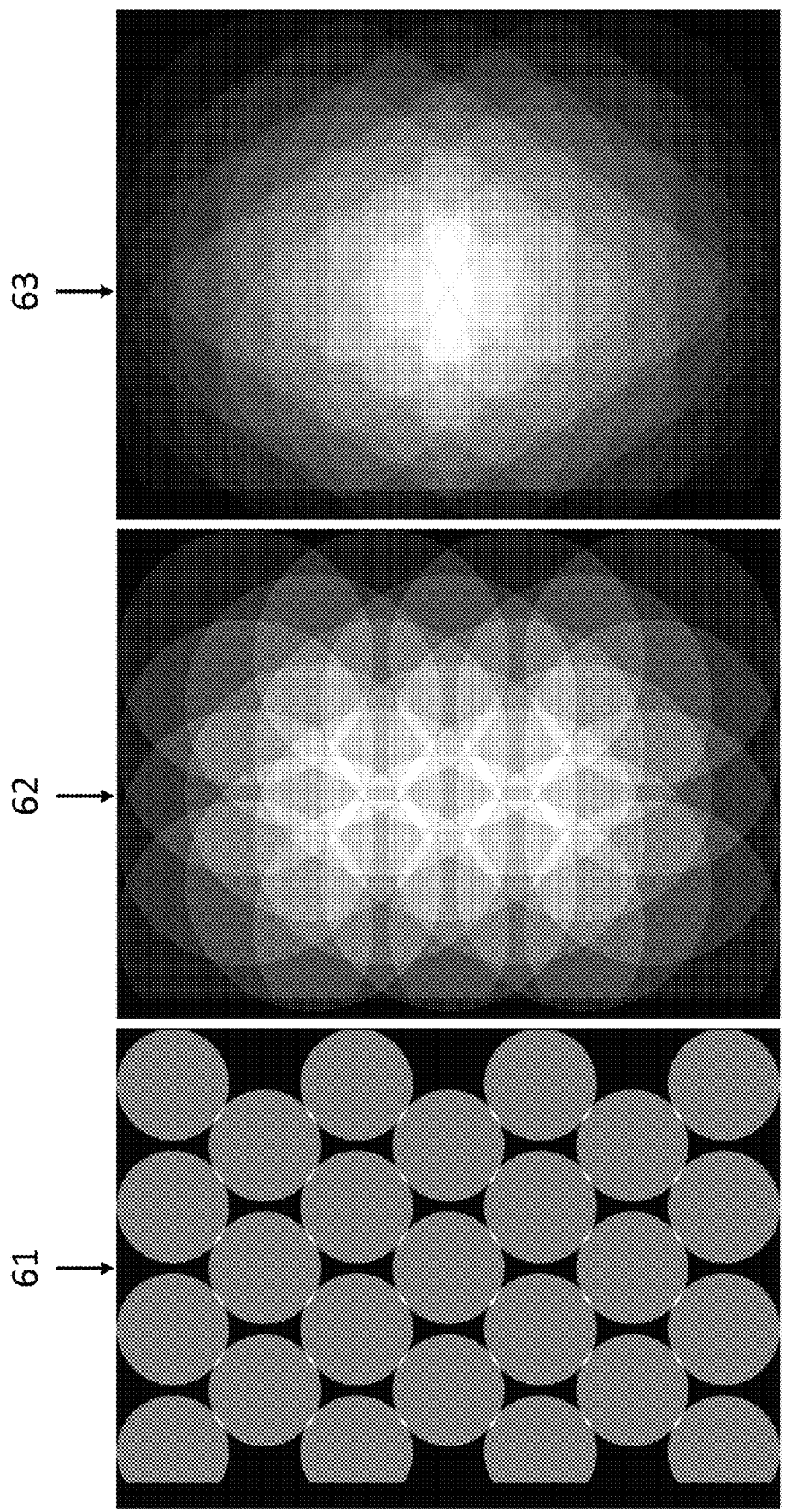
FIG. 2E illustrates the sample size on the object of each pinhole aperture (i.e. Field of View) with the object at the same distance from the pinhole panel as the detector is from the pinhole panel.
FIG. 2F illustrates the sample size on the object of each pinhole aperture (i.e. Field of View) with the object at a separation distance from the pinhole panel which is greater than the distance from the detector to the pinhole panel.
FIG. 2G illustrates the sample size on the object of each pinhole aperture (i.e. Field of View) with the object at a second distance from the pinhole panel which is greater than the separation distance (and the detector to the pinhole panel) illustrating the overlap on the object (of the samples/Field of Views) at different distances from the multiple pinholes.

This is further illustrated in FIGS. 2E to 2G. FIG. 2E illustrates the sample size on the object of each pinhole aperture (i.e. Field of View) with the object at the same distance from the pinhole panel as the detector is from the pinhole panel. FIG. 2F illustrates the sample size on the object of each pinhole aperture (i.e. Field of View) with the object at a separation distance from the pinhole panel which is greater than the distance from the detector to the pinhole panel. FIG. 2G illustrates the sample size on the object of each pinhole aperture (i.e. Field of View) with the object at a second distance from the pinhole panel which is greater than the separation distance (and the detector to the pinhole panel) thus further illustrating the overlap on the object (of the samples/Field of Views) at different distances from the multiple pinholes.

Thus in some embodiments, in addition to selecting a pinhole pattern/distribution that generates non overlapping images on the imaging surface, the pinhole pattern/distribution is also selected to ensure that the sampled region on the object through each pinhole overlaps with the other pinhole samples when the object is located at an object distance from the object greater than the separation distance ($d_O>d_D$). This means that the same region of the object can be represented in multiple pinhole projection images, and thus if the distance to the object is known, this can be used during synthesis of the composite image. The final composite image will have the resolution of the individual single pinhole apertures but with the increased X-ray backscatter dose corresponding to the sum of the overlapping signal sampling. As the object is located further from the pinhole panel 30 the sampling overlap on the object associated with pinhole images 44 increases and thus the amount of sampling overlap can be controlled through selection of the object distance $d_O$.

By ensuring the individual pinhole images 44 on the imaging surface 42 of the detector 40 remain completely separated (though control of the pinhole thickness, width and separation distance), the full resolution from each pinhole aperture is preserved. By ensuring the individual pinhole samples on the object overlap (though control of the object distance), the X-ray backscatter signal on the detector is increased and the signal strength from a given point of interest on the object can be increased by multiple factors compared to conventional pinhole imaging. This balance allows for the use of small pinholes to retain high resolution while also addressing the fundamental challenge of getting enough X-ray signal in a backscatter pinhole image.

By restricting the spread of the individual pinhole images, the detector can be moved closer to the pinhole panel and the region covered by each pinhole can be reduced. This increases the X-ray dose incident on the detector at each pinhole image because the X-ray dose reduces as a square of the distance. Additionally, this allows more pinholes to sample an object and the total dose on the detector scales linearly with the number of pinholes. This overcomes the primary limitation of conventional single pinhole imaging without incurring the loss of resolution and mathematical complexity of demultiplexing/deconvoluting overlapping images in coded aperture imaging.

As shown in FIG. 1A, an image 43 is formed on the imaging surface 42 and captured by the X-ray detector 40 and comprises a plurality of separate (or distinct) pinhole images 44. An image processor 50 is then used to process the image 43 to generate a synthetic combined image of the object 60. This processing may include identifying each of the plurality of pinhole images 44 in the image 43, and then combining or summing the individual pinhole images 44 to generate the synthetic combined image of the object 60 using knowledge of separation distance $d_D$, object distance $d_O$, pinhole thickness t, and pinhole width w, for example using measured data, entered data (via a user interface) or stored data. The image processor may identify the individual pinhole images based on spatial/geometrical information such as the separation distance, pinhole width and thickness which may be used to calculate the borders of the individual pinhole images 44 (e.g., as a set of pixel locations), or a memory may store the borders and image processor may look up the border information to extract out each individual pinhole image 44 from the overall image 43. In another embodiment the image processor may be configured to use an image processing method such as an object detection or segmentation method to identify each pinhole image 42 within the overall image 43. The image processor may implement a range of different image processing methods to generate the synthetic combined image. In one embodiment image processing comprises a simple scaling of the individual pinhole images 44 and averaging of overlapping (sampled) regions. In other embodiments more sophisticated methods may be used such as iterative reconstruction methods, optimization based methods, simulated annealing, probabilistic and expectation maximization methods. Iterative reconstruction methods may be used in which the summed/combined image is projected back through the pinholes and compared with the measured data to refine any inconsistencies between images. One advantage of using an iterative approach is that would be particularly beneficial in suppressing the imaging artifacts due to overlapping materials projecting differently into different pinholes based on the optics of the sampling. In some embodiments simulation based methods may be used to build a virtual model of the object including three dimensional structure and materials. The initial virtual model may be built using any available prior information on the object being imaged. The virtual model may be used to model backscatter and generate a model image which is combined with the observed image data. An optimization function may then be used to refine the model until a model, and synthetic image is obtained that best explains (of fits) the observed data. Further as the object will have a finite width, multiple images may be reconstructed by varying the object distance to estimate a different slice of the object to build up a three dimensional representation of the object. Reconstruction of the depth information is further improved by increasing the number of apertures to increase the overlap in the separate images.

As illustrated in FIG. 1B, a method 100 for generating a synthetic combined X-ray image of an object can be defined based on the above discussion. The method broadly comprises an illumination step 110, an image capture step 120, an object distance estimation step 130, and an image generation step 140. The illumination step 110 may comprise illuminating, using an X-ray source 10, an object 12 located an object distance $d_O$ from an X-ray imaging apparatus 20 to generate Compton backscattered X-rays towards a pinhole panel 30 located in the front surface of the X-ray imaging apparatus 20. The image capture step 120 may comprise capturing a plurality of pinhole images 44 on an imaging surface 42 of the X-ray imaging apparatus 40. The imaging surface 42 is located a separation distance $d_D$ behind the pinhole panel 30, and the pinhole panel 30 is comprised of a plurality of pinhole apertures 31, each passing through the pinhole panel 30 and having a predefined thickness t and a predefined width w. The pinholes are distributed over the pinhole panel in a predefined pattern 33, and the separation distance, thickness, width, and the predefined pattern of the pinhole apertures are selected to prevent overlap between any pair of pinhole images on the imaging surface 42. The X-ray imaging apparatus 20 is located such that the object distance is greater than the separation distance (i.e. $d_O > d_D$) so that for at least one pair of pinholes, each pinhole samples an overlapping portion of the object. That is each pinhole (or pinhole image) samples at least a portion of the object and the object distance is selected such that for at least one pair of pinholes, the two sample portions will share an overlapping portion.

The object distance estimation step 130 may comprise obtaining an estimate of the object distance and image generation step 140 may comprise generating, by an image processor, a synthetic combined image of the object using the plurality of pinhole images and the separation distance, object distance, pinhole thickness and pinhole width. The image processor 50 may be integrated into the X-ray apparatus 20 or be a separate computing apparatus which obtains the digital image 43 from an image detector 40 integrated in or housed in the X-ray apparatus 20. A memory operatively associated (including integrated in, or accessible by) with the image processor 50 may be used to store the separation distance, pinhole thickness and pinhole width for use during reconstruction of the synthetic image. The object distance may be measured by a user, a distance sensor, a range finder device, or stereoscopic camera system and supplied to the image processor by a user interface or be electronically communicated to the image processor from a sensor or range finder or otherwise stored in the associated memory. In one embodiment a default object distance is stored in a memory and obtaining an estimate of the object distance comprises looking up the default value stored in memory, and no separate measurement of the distance is obtained.

An embodiment of the invention, along with example data demonstrating backscatter image reconstruction, will now be described. A CMOS X-ray detector 40 with a 430 um CSI scintillator is used as the wide area digital detector; the CMOS detector has a 20 cm×20 cm imaging surface 42 with 0.1 mm pixel pitch. A Teledyne 160 kV 1 mA constant power X-ray source 10 is used to generate the X-ray signal. The pinhole panel 30 is a 6 mm thick steel plate with 25 1.5 mm diameter pinholes located in the front of the detector. The detector 40 is placed 100 mm behind the pinholes inside a shielded enclosure (i.e. $d_D$=0.1 m). An explosive simulant was created; this explosive simulant consisted of a 2 liter container of Urea pellets, a small circuit board, old cell phone, small battery, small 32 AWG wires connecting the battery to the board and cell phone, and a multiple screws and nails where all taped to the front of the urea container. This explosive simulant was placed inside a bag with clothing and imaged at several different distances ($d_O$) from the pinhole panel.

Figure 3B:
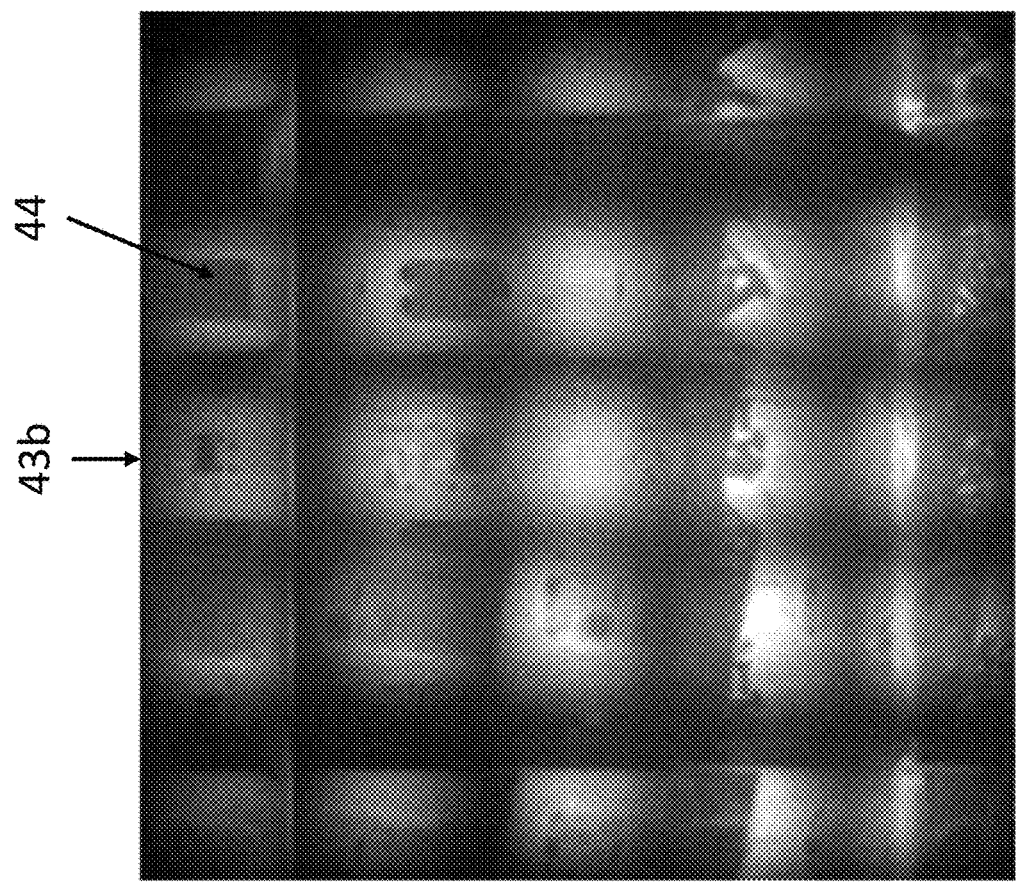
FIG. 3B is second image of the simulated explosive device captured using the embodiment of an X-ray imaging apparatus used in FIG. 3A with the object at a separation distance of 0.25 m from the pinhole panel.
Figure 3A:
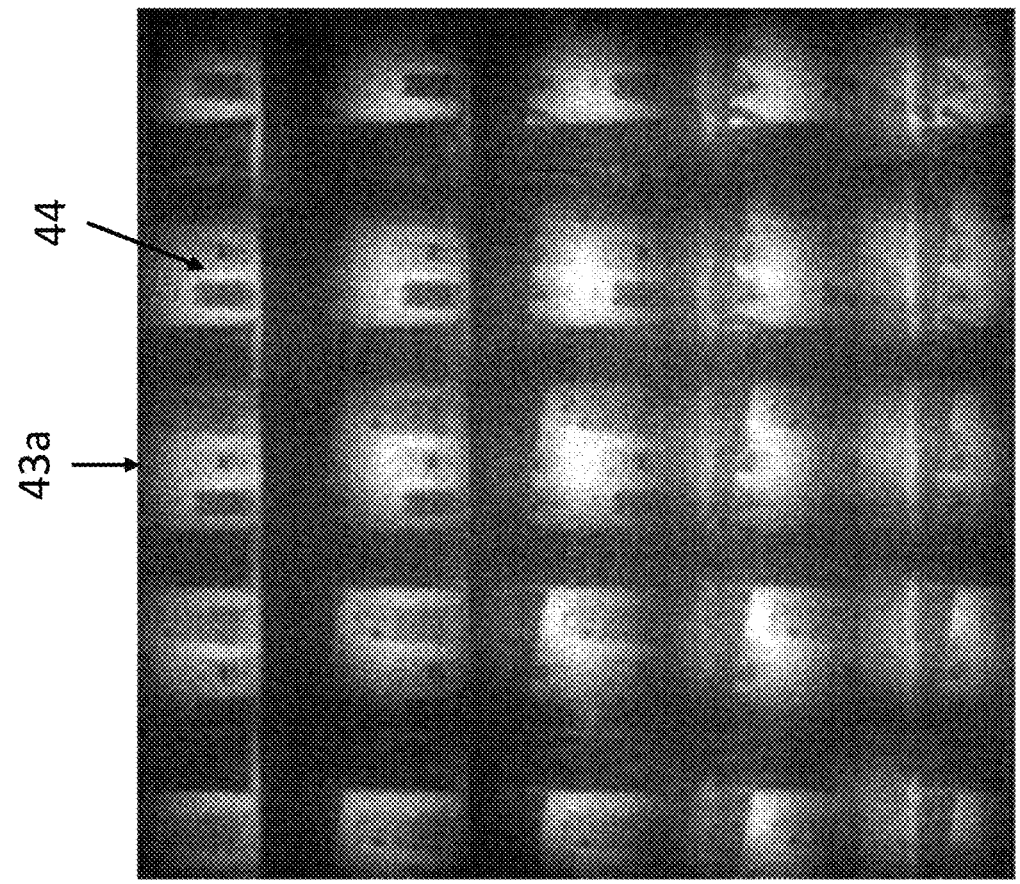
FIG. 3A is first image of a simulated explosive device captured using an embodiment of an X-ray imaging apparatus with a front aperture plate comprising 25 independent pinhole apertures and a 20 cm×20 cm digital detector with the object at a separation distance of 0.5 m from the pinhole panel.

The multiple non-overlapping backscatter pinhole images of the explosive simulant inside a bag are shown in FIGS. 3A and 3B. FIG. 3A is a first image 43*a* captured by the detector 40 showing the 25 individual pinhole images 44 obtained when the bag was placed 0.5 m in front of the pinhole panel 30 ($d_O$=0.5 m). As can be seen in FIG. 3A, there was considerable sampling overlap on the object and almost the entire simulated explosive can be seen in each of the 25 pinhole images 44. FIG. 3B is a second image 43*b* captured by the detector 40 showing the 25 individual pinhole images 44 obtained when the object distance was halved such that the bag was only 0.25 m in front of the pinhole panel 61 ($d_O$=0.25 m). As can be seen in FIG. 3B, each pinhole aperture 31 now sampled a smaller portion of the simulated explosive. Both images were taken at the same total X-ray dose of 160 kV 1 mA. The noise in the first image 43*a* is clearly higher due to the increased distance from the X-ray source 10 to the object 12 and from the object 12 back to the imaging apparatus 20 (and detector 40). The resolution in the second closer image 43*b* is clearly better due to the geometrical effects associated with a reduced object distance (as the fixed number of detector pixels sample a smaller region on the object).

Figures 4A, 4B:
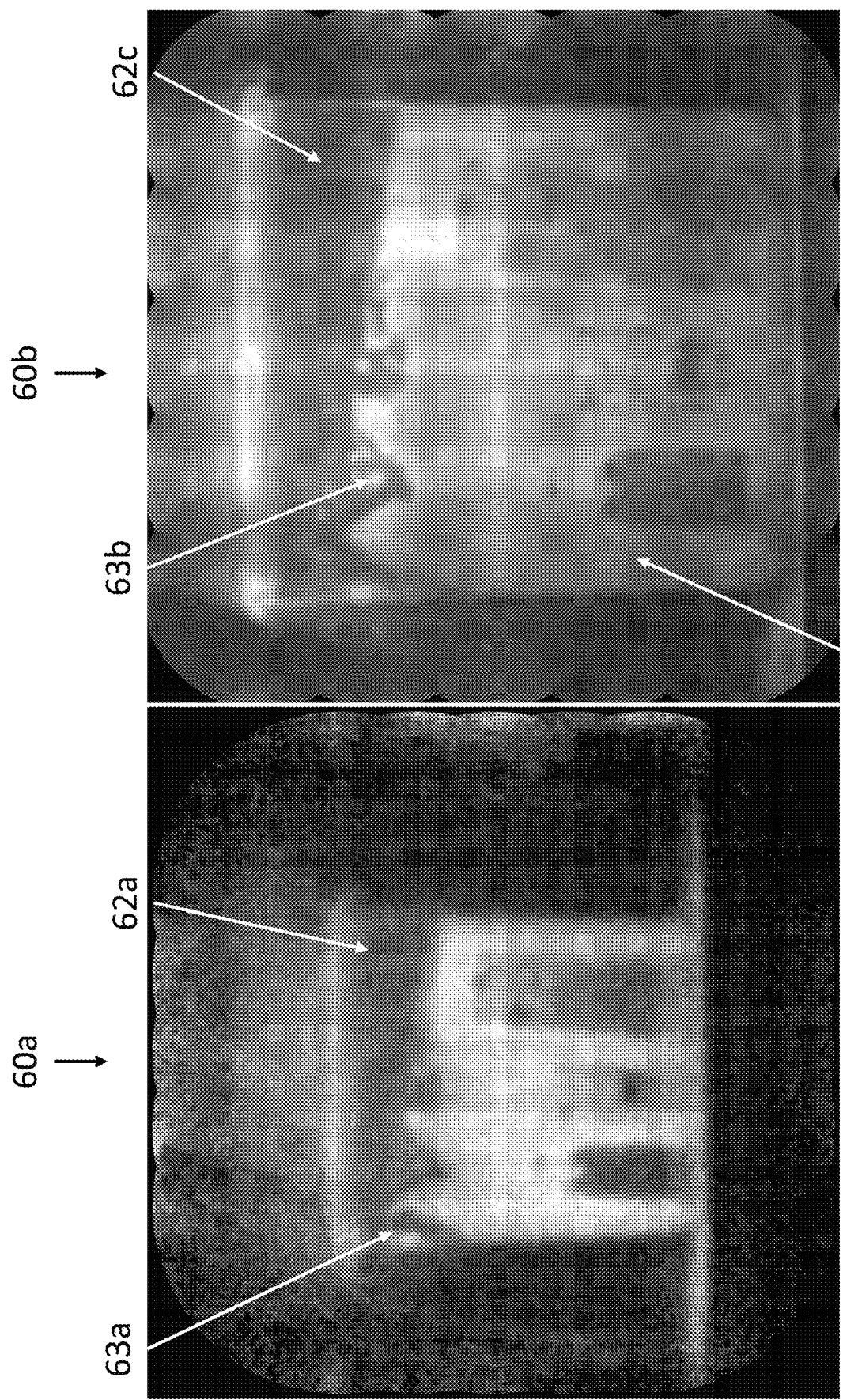
FIG. 4A is the signal reconstructed backscatter image of the simulated explosive device from all the individual pinhole apertures in FIG. 3A (object at the separation distance).
FIG. 4B is the signal reconstructed backscatter image of the simulated explosive device from all the individual pinhole apertures in FIG. 3B (object at the second distance).

FIGS. 4A and 4B show the reconstructed synthetic images obtained by combining the multiple individual images 44 shown in each of FIGS. 3A and 3B (respectively). FIG. 4A shows a single synthetic (composite) image 60a obtained by using an image processor to sum together all 25 pinholes images 44 shown in FIG. 3A (with the object at $d_O$=0.5 m). In this case there is significant overlap between sampling of the object by the pinholes 31 such that the dose has been increased in the combined image 60a by a factor of 10 relative to a single pinhole image (For example a single large pin hole could be taken by using a hole with the same 1.5 mm diameter but located in a thinner plate (e.g. 2 mm of lead) and increasing the distance, but this arrangement would have much less dose). Similarly FIG. 4B shows a single synthetic (composite) image 60b obtained by using an image processor to sum together all 25 pinholes images 44 shown in FIG. 3B (with the object at $d_O$=0.25 m). In this case there is smaller overlap between sampling of the object by the pinholes 31 and thus the X-ray dose has only been increased by a factor of between 2 and 3. In both images, the resolution in the small pinhole images has been preserved and components such as small wires (62a, and 62b) and screws (63a, 63b, and 63c) can be readily identified. Both synthetic images 60a and 60b are reconstructed using 0.1 mm pixels to retain the resolution in the pinhole images.

The image reconstruction method used in the demonstrated embodiment is a simple scaling of the individual pinhole images 44 and averaging of overlapping (sampled) regions. Each pinhole image is scaled by a magnification factor, M, which is the ratio of the distance from the pinhole panel to the object relative to the distance from the pinhole panel to detector (i.e. $M=d_O/d_D$). Thus with a fixed pinhole to detector separation distance $d_D$=0.1 m and an object distance of $d_O$=0.5 m this is a 5× magnification, and at an object distance of $d_O$=0.25 m this is a 2.5× magnification. Each pinhole image is then up-sampled, base on the magnification, to retain the 0.1 mm pixel resolution. The signal from pixels of the object corresponding to overlapping samples of the object in the pinhole images 44, which can be determined using the known object distance and pinhole pattern, is then averaged together to form the final signal at a pixel.

It will be appreciated that this method is an exemplary method and there are many different ways to reconstruct the individual pinhole images, including the use of more sophisticated image processing methods. Such methods may include iterative reconstruction methods where the summed image is projected back through the pinholes and compared with the measured data to refine any inconsistencies between images. One advantage of using an iterative approach is that would be particularly beneficial in suppressing the imaging artifacts due to overlapping materials projecting differently into different pinholes based on the optics of the sampling.

It will be appreciated that there are many different ways to implement embodiments of an imaging apparatus or a method for generating a synthetic combined X-ray image of an object based as described above.

In one embodiment, the X-ray source is a cold-cathode Carbon Nanotube (CNT) based X-ray source. The size of the imaging system will be determined by the size of the X-ray detector 40, the housing 21 (or radiation shielded enclosure 28), and the X-ray tube 10. Conventional X-ray tubes are large and complex and require additional X-ray radiation shielding. CNT based X-ray tubes significantly reduce the size and complexity of the X-ray source without compromising the X-ray power or dose. Reduction and simplification of the X-ray tube will enable a smaller, lighter, and more cost-effective overall imaging system.

In one embodiment, the X-ray source 10 is a conventional X-ray source capable of delivering the current and energy required for the backscatter application. In one embodiment for use in Explosive Ordinance Detection (EOD), counter-terrorism, and custom and boarder control applications the x-ray backscatter is delivered in a range from 100 kV to 160 kV and a current of between 0.1 mA to 10 mA. If the size of the system is not a concern or the X-ray flux and energy requirements are low, a conventional heated cathode X-ray tube can be used to provide the source X-rays.

In one embodiment, the X-ray detector 40 is a CMOS digital detector coupled to an X-ray scintillator. CMOS X-ray detectors have been shown to be highly effective in measuring low intensity X-ray signals. The backscatter signal will also be low intensity compared to conventional transmission detectors and a CMOS detector will enable higher image quality at low dose.

In one embodiment, the X-ray detector 40 is photon-counting large area detector. Photon counting detectors convert incident X-ray photons directly into an electrical current and can be configured to also measure the X-ray energy of the incident X-rays. Energy information about the backscatter increases the material specificity in the backscattered signal because the angle of Compton scatter is based on both the material atomic structure and energy of the X-rays. Even without energy information, a photon counting detector may be used to enhance the image quality due to the high dose efficiency of these detectors at low dose.

In one embodiment, the X-ray detector 40 is a photodiode array coupled to an X-ray scintillator. Photodiode digital X-ray detectors are fast becoming commodity items and are the most cost-effective detector. The cost-effective solution can be used and the X-ray source increased in flux or energy to compensate for the loss in low dose efficiency.

In one embodiment, the object distance $d_O$ is manually obtained or set by the operator and provided, for example by a user interface, to the image processor or associated image processing software executing on the image processor. In one embodiment the object distance $d_O$ is automatically obtained by a distance sensor, for example at the time of capture of the X-ray image, and stored or provided to the image processor for use during image synthesis.

In one embodiment, the image processor (or image processing software executing on the image processor) generates a real-time synthetic image of the object which is displayed to the operator, and the operator can manually or automatically adjust the object distance to allow multiple images to be generated to allow selection of a best image (for example a sharp image with detail). In some embodiments the reconstruction software continuously reconstructs synthetic combined image at different object distances until the operator has selected the optimal distance/image. In some embodiments the X-ray imaging apparatus stores a default object distance (e.g. 0.5 m) which is varied until an optimal distance/image is obtained. In this embodiment obtaining an estimate of the object distance thus comprises looking up the default value stored in memory, and no separate measurement of the distance is obtained. This distance setting feature may also be used to provide information to the operator about the depth of an object of interest.

In one embodiment, the X-ray apparatus automatically determines the object distance using a distance or proximity sensor integrated into the imaging system. The proximity sensor estimates the distance to the scanned object and feeds this information to the image reconstruction software. In some embodiments a stereoscopic camera system may be used to capture optical images of the object and estimate the distance using known properties of the stereoscopic camera system. This estimated object distance may be used as a starting distance and the operator allowed to adjust the distance to see objects deeper in the scanned object.

The one embodiment the radiation shielded enclosure 28, or housing 21, may be formed of one or more X-ray attenuating materials such as lead, steel, Aluminum, metal alloys, or plastics and polymers incorporating radiation absorbing compounds such as Barium, Bismuth, and Tungsten salts. Different materials may be used for different parts of the enclosure and thickness of different components may be varied to provide the required shielding. In some embodiments the pinhole panel 30 is formed of a thick single plate of an X-ray attenuating material such as lead, Aluminum or steel (including alloys). In other embodiments the pinhole panel 30 is a composite panel formed of several sections and/or several materials, such as laminated layers, such that the composite panel acts as X-ray attenuating material. The panel may be of a constant thickness or it may be of variable thickness provided all parts provide the required shielding/X-ray attenuation. The pinhole panel may be a steel (or metal) plate forming the front surface of the enclosure or it may be integrated into the front surface of the housing. For example the housing could be constructed with a wide area aperture in the front surface over which the pinhole panel is secured or fastened.

The material may be selected or configured to attenuate incident X-rays of a threshold energy to a below a threshold flux level, for example by selection of shielding material and thickness. The threshold energy of the X-rays may be the energy of X-rays generated by the intended X-ray source 10, or the X-ray source 10 may be operated or configured to generate X-rays at an energy less than or equal to threshold energy. In some embodiments, the front panel of the radiation shielded enclosure 28 is formed of a first material or materials rated to attenuate X-rays of the threshold energy (e.g. Compton backscattered X-rays from the X-ray source), and the remaining sides of the enclosure, or at least those in the shadow of the front panel with respect to backscattered X-rays from the object, are rated to attenuate X-rays at a second threshold energy level lower than the first energy level, for example an energy based on the average background radiation.

In one embodiment the X-ray attenuation plate is a composite plate 30' comprised of two different materials each having different X-ray attenuation properties and thicknesses. Further each pinhole aperture 31 is a composite pinhole aperture 31' comprising two overlapping pinholes. FIG. 5A is a side view of a composite pinhole 31' in a composite X-ray attenuation plate 30 according to an embodiment. The first plate 30a' is formed from a very thin dense highly attenuating material such as lead or tungsten (thus having a small thickness $t_1$) and has a first pinhole 31a' with a small width ($w_1$). In comparison, the second plate 30b' is formed from a thicker less dense material such as steel (thus having a larger thickness $t_2>t_1$) and has a second pinhole 31b' with a comparatively wide width ($w_2>w_1$). The first pinhole 31a provides a high-resolution pinhole aperture whilst the second pinhole 31b' restricts the spread of the pinhole image on the detector to ensure each pinhole image does not overlap (i.e. the second pinhole acts as an optical stop). This is further illustrated in FIG. 5B is a schematic illustration of the comparative image sizes that would be generated solely by the first pinhole 31a' and by the composite pinhole as illustrated in FIG. 5A which shows the resultant pinhole image I has a diameter smaller than the image I' that would otherwise result from use of only the first pinhole 31a' creating an excluded annular region I. This approach balances dose on the detector, resolution through the pinhole, and overlap between pinhole images, as the use of the second pinhole to stop the image that would be formed by the first pinhole allows a greater number of (non-overlapping) images to be packed onto the (2D) detector surface 42.

The image processor 50 may be an embedded image processor integrated into the X-ray detector 40 and/or imaging apparatus 20, or it may be a separate computing apparatus which receives the image (containing the plurality of pinhole images) 42 captured by the digital X-ray detector 40 and which contains image processing hardware, and/or executes image processing software to generate the synthetic image 60. The image processor may be configured (for example by appropriate software) to identify each of the plurality of pinhole images in the image captured by the digital X-ray detector and generate the synthetic combined image of the object by combining the plurality of pinhole images. The image processor 50 may be a cloud-based computing system that receives an image sent by the digital detector, or a local computing apparatus that receives the image from the digital detector 40. The image processor may be a computing apparatus comprises a central processing unit (CPU), a memory, and an Input/Output (or Communications) interface, and may include a graphical processing unit (GPU), and input and output devices. The CPU may comprise an Arithmetic and Logic Unit (ALU) and a Control Unit and Program Counter element. The GPU may comprise a highly parallel architecture configured to perform image and graphics related calculations. The memory may be operatively coupled to the processor(s) and may comprise RAM and ROM components and secondary storage components such as solid state disks and hard disks, which may be provided within or external to the image processor 50. The Input/Output Interface may comprise a network interface and/or communications module for communicating with an equivalent communications module in another apparatus using a predefined communications protocol (e.g. Bluetooth, Zigbee, IEEE 802.15, IEEE 802.11, TCP/IP, UDP, etc.). Input and output devices may be connected via wired or wireless connections. The Input/Output interface may be used to communicate with other computing apparatus, for example to obtain an object distance estimate. Input and output devices may comprise a keyboard, a mouse, stereoscopic camera, and a display apparatus such as a flat screen display (e.g. LCD, LED, plasma, touch screen, etc.), a projector, CRT, etc.

The image processor may comprise a single CPU (core) or multiple CPU's (multiple core), or multiple processors including CPUs and GPUs. The image processor 50 may be computing apparatus such as desktop computer, mobile computer, server, and may use be may be part of a distributed (cloud) computing apparatus. The memory may comprise instructions to cause the processor to execute a method described herein. The memory may be used to store the operating system and additional software modules or instructions, for example developed using high level languages such as python, C++ or JAVA. The memory may store image processing libraries and software such as OpenCV or Scikit-image. The processor(s) may be configured to load and execute the software modules or instructions stored in the memory. The synthetic image 60 may be exported or saved to local or external storage, including cloud based storage.

Embodiments of the X-ray imaging apparatus devices can be used to generate a synthetic combined X-ray image of an object. Embodiments of the X-ray imaging apparatus use a digital detector with two-dimensional (i.e. Area) imaging surface in place of conventional scintillators and photo-multiplier tubes. In some embodiments the two dimensional imaging surface is a flat imaging surface (e.g. a flat panel detector with x and y coordinates), however in other embodiments the imaging surface may be a curved two-dimensional surface e.g. the imaging surface has a constant radius of curvature such that the two dimensional surface is a part of the surface of a sphere (a spherical sector), with the two dimensions being orthogonal angular coordinates inclination and azimuth ($\theta$, $\phi$). That is the X-ray detector may have a two dimensional imaging surface in the form of a flat panel or a curved panel. A pinhole panel comprising X-ray attenuation material such as metal plate, though which a plurality of pinhole apertures pass through is located in the front surface of the X-ray imaging apparatus. The separation distance between the pinhole panel and imaging surface of the X-ray imaging apparatus, along with the pinhole thickness, pinhole width, and the predefined pattern of the pinhole apertures are selected to prevent overlap between any pair of pinhole images on the imaging surface. That is the multiple pinhole apertures 31 are arranged in a specific pattern/distribution so as to explicitly not overlap on the imaging surface 42 of the detector 40. Further the X-ray imaging apparatus may be located at an object distance greater than the separation distance so that individual pinholes (or pinhole images) sample overlapping portions of the object.

Embodiments may be used to combine the increased X-ray signal obtained with coded apertures with the high image resolution and image quality of a single pinhole aperture, whilst avoiding the mathematical complexity of demultiplexing/deconvoluting overlapping images associated with the use of coded apertures. This approach enables the design of a smaller and lighter high-resolution backscatter imaging system because the high-power X-ray source is no longer constrained by the weight and complexity of the pencil beam collimator/coded aperture. Embodiments of the X-ray imaging apparatus may be used for remote detection of explosive devices (e.g. I.E.D.s), narcotics, or organic substances stored or located within bags, packages, or equipment, for example in EOD, customs and border control, and first responder applications.

Those of skill in the art would understand that information and signals may be represented using any of a variety of technologies and techniques. For example, data, instructions, commands, information, signals, bits, symbols, and chips may be referenced throughout the above description may be represented by voltages, currents, electromagnetic waves, magnetic fields or particles, optical fields or particles, or any combination thereof.

Those of skill in the art would further appreciate that the various illustrative logical blocks, modules, circuits, and algorithm steps described in connection with the embodiments disclosed herein may be implemented as electronic hardware, computer software or instructions, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The steps of a method or algorithm described in connection with the embodiments disclosed herein may be embodied directly in hardware, in a software module executed by a processor, or in a combination of the two. For a hardware implementation, processing may be implemented within one or more application specific integrated circuits (ASICs), digital signal processors (DSPs), digital signal processing devices (DSPDs), programmable logic devices (PLDs), field programmable gate arrays (FPGAs), processors, graphical programming units (GPUs), controllers, micro-controllers, microprocessors, other electronic units designed to perform the functions described herein, or a combination thereof. Software modules, also known as computer programs, computer codes, or instructions, may contain a number a number of source code or object code segments or instructions, and may reside in any computer readable medium such as a RAM memory, flash memory, ROM memory, EPROM memory, registers, hard disk, a removable disk, a CD-ROM, a DVD-ROM, a Blu-ray disc, or any other form of computer readable medium. In some aspects the computer-readable media may comprise non-transitory computer-readable media (e.g., tangible media). In addition, for other aspects computer-readable media may comprise transitory computer-readable media (e.g., a signal). Combinations of the above should also be included within the scope of computer-readable media. In another aspect, the computer readable medium may be integral to the processor. The processor and the computer readable medium may reside in an ASIC or related device. The software codes may be stored in a memory unit and the processor may be configured to execute them. The memory unit may be implemented within the processor or external to the processor, in which case it can be communicatively coupled to the processor via various means as is known in the art.

Further, it should be appreciated that modules and/or other appropriate means for performing the methods and techniques described herein can be downloaded and/or otherwise obtained by computing device. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a computing device can obtain the various methods upon coupling or providing the storage means to the device. Moreover, any other suitable technique for providing the methods and techniques described herein to a device can be utilized.

In one form the invention may comprise a computer program product for performing the method or operations presented herein. For example, such a computer program product may comprise a computer (or processor) readable medium having instructions stored (and/or encoded) thereon, the instructions being executable by one or more processors to perform the operations described herein. For certain aspects, the computer program product may include packaging material.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

As used herein, the term "estimating" and "determining" encompasses a wide variety of actions. For example, "estimating" and "determining" may include calculating, computing, processing, deriving, investigating, looking up (e.g., looking up in a table, a database or another data structure), ascertaining and the like. Also, "estimating" and "determining" may include receiving (e.g., receiving information), accessing (e.g., accessing data in a memory) and the like. Also, "estimating" and "determining" may include resolving, selecting, choosing, establishing and the like.

As used herein, a phrase referring to "at least one of" a list of items refers to any combination of those items, including single members. As an example, "at least one of: a, b, or c" is intended to cover: a, b, c, a-b, a-c, b-c, and a-b-c.

It will be understood that the terms "comprise" and "include" and any of their derivatives (e.g. comprises, comprising, includes, including) as used in this specification is to be taken to be inclusive of features to which the term refers, and is not meant to exclude the presence of any additional features unless otherwise stated or implied.

The reference to any prior art in this specification is not, and should not be taken as, an acknowledgement of any form of suggestion that such prior art forms part of the common general knowledge.

It will be appreciated by those skilled in the art that the disclosure is not restricted in its use to the particular application or applications described. Neither is the present disclosure restricted in its preferred embodiment with regard to the particular elements and/or features described or depicted herein. It will be appreciated that the disclosure is not limited to the embodiment or embodiments disclosed, but is capable of numerous rearrangements, modifications and substitutions without departing from the scope as set forth and defined by the following claims.

The invention claimed is:

1. An X-ray imaging apparatus, comprising:
    a digital X-ray detector comprising an imaging surface; and
    a radiation shielded enclosure housing the digital X-ray detector and comprising a pinhole panel located in a front surface of the housing with a plurality of pinhole apertures each passing through the panel and having a predefined thickness and a predefined width, wherein the imaging surface is located a separation distance from the pinhole panel, and the radiation shielded enclosure is configured to restrict X-ray radiation incident on the imaging surface to X-rays passing through the plurality of pinhole apertures such that each pinhole aperture generates a respective pinhole image on the imaging surface, and the plurality of pinhole apertures are distributed over the pinhole panel in a predefined pattern and configured such that a diameter of the pinhole image is determined by the separation distance, the thickness and the width of the corresponding pinhole aperture, and the separation distance, thickness, width, and the predefined pattern of the pinhole apertures are selected to prevent overlap between any pair of pinhole images on the imaging surface; and
    wherein, in use, an X-ray source illuminates an object located an object distance from the pinhole panel to generate Compton backscattered X-rays towards the X-ray imaging apparatus, and the digital X-ray detector is configured to capture a plurality of pinhole images on the imaging surface which are combined by an image processor to generate a synthetic combined image of the object.

2. The apparatus as claimed in claim 1, wherein the object distance is greater than the separation distance and each pinhole images samples at least a portion of the object and the object distance is selected such that each sample portion overlaps at least one other sample portion.

3. The apparatus as claimed in claim 1, wherein the X-ray imaging apparatus further comprises the image processor which is configured to identify each of the plurality of pinhole images in an image captured by the digital X-ray detector and generate the synthetic combined image of the object by combining the plurality of pinhole images.

4. The apparatus as claimed in claim 3, wherein the apparatus further comprises a distance sensor or proximity sensor configured to determine the object distance from the pinhole panel and the object, and the object distance is provided to the image processor for use in generating the synthetic combined image.

5. The apparatus as claimed in claim 3, wherein the image processor is configured to generate the synthetic combined image using an iterative reconstruction approach to account for a depth information inherent in the plurality of pinhole images due to a depth of the object.

6. The apparatus as claimed in claim 1, wherein the digital X-ray detector is a CMOS, photon counting, or Photodiode array digital detector.

7. The apparatus as claimed in claim 1, wherein the pinhole panel comprises of multiple stacked pinholes of different widths and thicknesses to balance radiation shielding, image resolution, and pinhole image size on the imaging surface.

8. The apparatus as claimed in claim 1, further comprising an X-ray source configured to illuminate an object located an object distance from the pinhole panel to generate Compton backscattered X-rays towards the X-ray imaging apparatus.

9. The apparatus as claimed in claim 8, wherein the X-ray source is a Carbon Nanotube X-ray source.

10. A method for generating a synthetic combined X-ray image of an object, comprising:
    illuminating, using an X-ray source, an object located an object distance from an X-ray imaging apparatus to generate Compton backscattered X-rays towards a pinhole panel located in a front surface of the X-ray imaging apparatus;
    capturing a plurality of pinhole images on an imaging surface of the X-ray imaging apparatus, wherein the imaging surface is located a separation distance behind the pinhole panel, and the pinhole panel is comprised of a plurality of pinhole apertures, each passing through the pinhole panel and having a predefined thickness and a predefined width, and are distributed over the pinhole panel in a predefined pattern, and the separation distance, thickness, width, and the predefined pattern of the pinhole apertures are selected to prevent overlap between any pair of pinhole images on the imaging surface, and the X-ray imaging apparatus is located such that the object distance is greater than the separation distance so that for at least one pair of pinholes, each pinhole samples an overlapping portion of the object;
    obtaining an estimate of the object distance; and
    generating, by an image processor, a synthetic combined image of the object using the plurality of pinhole images and the separation distance, object distance, pinhole thickness and pinhole width.

11. The method as claimed in claim 10, wherein obtaining an estimate of the object distance comprises measuring the object distance using a range finder, distance sensor, proximity sensor or stereoscopic camera.

12. The method as claimed in claim 10, wherein the pinhole panel is comprised of multiple stacked pinholes of different widths and thicknesses selected to balance radiation shielding, image resolution, and pinhole image size on the imaging surface.

13. The method as claimed in claim 10, wherein generating the synthetic combined image is performed using an iterative reconstruction method which takes into account a depth information inherent in the plurality of pinhole images due to a depth of the object.

* * * * *